United States Patent [19]

Jonas et al.

[11] Patent Number: 5,104,881
[45] Date of Patent: Apr. 14, 1992

[54] 2-ARYLIMIDAZOPYRIDINES

[75] Inventors: Rochus Jonas, Darmstadt; Klaus Minck, Ober-Ramstadt; Hans J. Enenkel, Darmstadt; Hans-Jochen Schliep, Traisa, all of Fed. Rep. of Germany

[73] Assignee: Merck Patent Gesellschaft Mit Beschrankter Haftung, Darmstadt, Fed. Rep. of Germany

[21] Appl. No.: 595,010

[22] Filed: Mar. 29, 1984

Related U.S. Application Data

[62] Division of Ser. No. 409,471, Aug. 19, 1982, Pat. No. 4,616,090.

[30] Foreign Application Priority Data

Aug. 19, 1981 [DE] Fed. Rep. of Germany ....... 3132754
Oct. 1, 1981 [DE] Fed. Rep. of Germany ....... 3139064

[51] Int. Cl.$^5$ ................. A61K 31/435; C07D 471/04
[52] U.S. Cl. ..................................... 514/303; 546/118
[58] Field of Search ................. 546/118; 424/256; 514/303

[56] References Cited

U.S. PATENT DOCUMENTS

| | | | |
|---|---|---|---|
| 3,985,891 | 11/1976 | Kutter et al. | 424/263 |
| 4,281,005 | 7/1981 | Baldwin | 424/263 |
| 4,327,100 | 4/1982 | Austel et al. | 546/118 |
| 4,353,909 | 10/1982 | Diederen et al. | 546/118 |
| 4,396,764 | 8/1983 | Tanaka et al. | 546/194 |
| 4,421,755 | 12/1983 | Benedikter et al. | 514/303 |
| 4,603,139 | 7/1986 | King | 514/337 |
| 4,758,574 | 7/1988 | Robertson et al. | 514/303 |
| 4,904,785 | 2/1990 | Robertson et al. | 546/118 |

FOREIGN PATENT DOCUMENTS

| | | |
|---|---|---|
| 2305339 | 8/1974 | Fed. Rep. of Germany . |
| 2641060 | 3/1978 | Fed. Rep. of Germany . |
| 150308 | 7/1970 | New Zealand . |
| 566842 | 7/1977 | U.S.S.R. . |

OTHER PUBLICATIONS

Middleton et al., Mutation Research, 78(1980) 323-329
CPI/WPI, Accession Number Index (V) 1978, Derwent.
Dorland's Illustrated Medical Dictionary, 26th Ed. 1981, p. 670.
Derwent Abstract (SU-566-842) 43447A/24.
Thornber Chemical Society Reviews vol. 8 No. 4 1979.
Drug of the Future vol. VI. No. 7 1981.
Spector et al. J. Het. Chem. vol. 6 p. 605 1969.
"Improved Preparation of Pyrido 3',4'(4',3'):4,5 Imidazo 1,2-c 1,2,3 Benzotriazines", CCPI Briefs, Org. Prep. Proced. Int. 12(3 4) (1980) pp. 234-237.
Chem. Abs. 96:68900f.
Haskell et al., "Neuraminidase Inhibition and Viral Chemotherapy" J. Med. Chem., 13:4 (1970), 697-703.
Middleton J. Het. Chem., 17, 1,757-1,760 (1980) Drugs of the Future, 6, 421-422 (1981).
European Search Report Appln. No. EP 82 106 638 dated Nov. 19, 1982.
Christopher A. Lipinski, "Bioisosterism in Drug Design," Annual Reports in Medicinal Chemistry 21, pp. 283-291 (1986).

Primary Examiner—Jane T. Fan
Attorney, Agent, or Firm—Millen, White & Zelano

[57] ABSTRACT

New 2-arylimidazopyridines of the general formula I

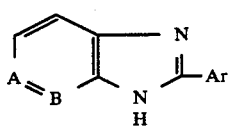

I wherein
—A=B— is (a) —CH=N— or (b) N=CH—,
Ar is a phenyl radical, which, in case (a), is substituted by one or two alkynyloxy, cyanomethoxy, carboxymethoxy, and/or alkyloxycarbonylmethoxy groups, and can be substituted by one or two additional hydroxyl, alkyloxy, alkenyloxy and/or alkynyloxy groups, or which in case (b), is substituted by one to three hydroxyl, mercapto, and/or —Z—R groups, Z is —O—, —S— or —SO— and R is alkyl, alkenyl, alkynyl, hydroxyalkyl, cyanomethyl, carboxymethyl or alkyloxycarbonylmethyl, the alkyl, alkenyl, alkynyl and hydroxyalkyl groups each having up to 5 C atoms, but wherein in case (b), the phenyl radical is only substituted by hydroxyl or methoxy groups if it has at the same time at least one other substituent differing from these, and their physiologically acceptable salts show positive inotropic effects.

31 Claims, No Drawings

2-ARYLIMIDAZOPYRIDINES

This is a continuation, division, of application Ser. No. 409,471 filed Aug. 19, 1982 now U.S. Pat. No. 4,616,090 issued Oct. 7, 1986.

BACKGROUND OF THE INVENTION

The present invention relates to new 2-arylimidazopyridines.

Some 2-arylimidazopyridines are known from German Offenlegungsschrift 2,305,339. Similar compounds are also described in the Soviet Union Patent 566,842, for example those which correspond to formula Ib below, but wherein a phenyl or a p-methoxyphenyl group is present instead of Ar. Furthermore, 2-o-hydroxyphenylimidazo(4,5-c)-pyridine is known from J. Het. Chem., volume 17, pages 1,757–1,760 (1980).

SUMMARY OF THE INVENTION

It is an object of the present invention to provide new compounds with valuable properties, in particular those which can be used for the preparation of medicaments.

These objects have been achieved by providing compounds of formula I.

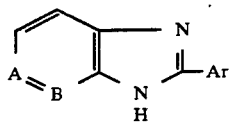

wherein

—A═B— is (a) —CH═N— or (b) —N═CH—;

Ar is phenyl, which, in case (a), is substituted by one or two alkynyloxy, cyanomethoxy, carboxymethoxy, and/or alkyloxycarbonylmethoxy groups, and can also be substituted by one or two hydroxyl, alkyloxy, alkenyloxy and/or alkynyloxy groups, or which, in case (b), is substituted by one to three hydroxyl, mercapto and/or —Z—R groups, Z being —O—, —S— or —SO— and R being alkyl, alkenyl, alkynyl, hydroxyalkyl, cyanomethyl, carboxymethyl or alkyloxycarbonylmethyl, all alkyl, hydroxyalkyl, alkenyl and alkynyl portions each having up to 5 C atoms, but wherein, in case (b), the phenyl radical is only substituted by hydroxyl or methoxy groups if it also has at least one other substituent differing from these, and their physiologically acceptable salts.

DETAILED DISCUSSION

In the synthesis of these new compounds, only one form is produced, for which the structure of the 3H-imidazopyridines (I) is given, specifically that of the 3H-imidazo(4,5-b)pyridines (Ia; compare "The Ring Index", 2nd Edition, American Chemical Society, 1960, No. 1,193) or that of the 3H-imidazo(4,5-c)pyridines (Ib; compare "The Ring Index" l.c., No. 1,195):

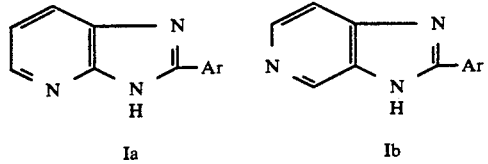

The structure of the tautomeric 1H-imidazopyridines I', specifically that of the 1H-imidazo(4,5-b) pyridines (Ia'; "The Ring Index", l.c., No. 1,192) or that of the 1H,imidazo(4,5-c)pyridines (Ib'; "The Ring Index", l.c., No. 1,194)

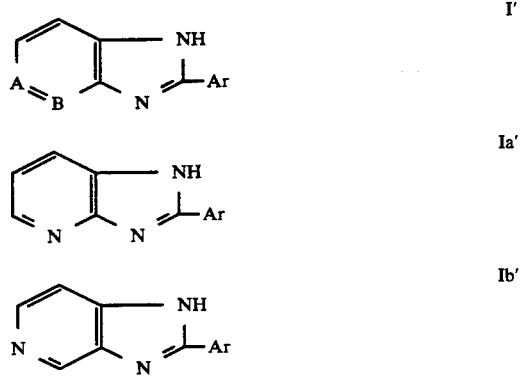

is, however, equally possible. The compounds are therefore designated in the foregoing and subsequent text as "imidazopyridines" or "imidazo(4,5-b)pyridines" or "Imidazo(4,5-c)pyridines" or "compounds of formula I" or "compounds of formula Ia" or "compounds of formula Ib"; however these designations are intended to include both the 3H-tautomers, I or Ia or Ib, and also the 1H-tautomers, I' or Ia' or Ib'.

It has been found that these compounds possess valuable pharmacological properties together with good tolerance. In particular, they exhibit an effect on the blood pressure and on the force of myocardial contraction (positive inotropic effect) and an ulcer effect, e.g., antihypertensive and antiulcerogenic effects.

The effects on blood pressure and the heart can be demonstrated, for example, on anaesthetized or conscious dogs, cats, monkeys or minipigs, and the positive inotropic effect on isolated heart preparations (for example atrium, papillary muscle or perfused complete heart) of rat, guinea pig or cat, for example by fully conventional methods as described in Arzneimittelforschung, volume 31 (I) No. Ia (1981), pages 141 to 170.

Thus, the compounds can be used as active ingredients in medicaments in human and veterinary medicine, e.g., for administration in the above purposes, to mammals including humans. In addition, they can be used as intermediate products for the preparation of other active ingredients or medicaments.

In the compounds of formula I, the phenyl group can be substituted once (in the o-, m- or p-position), twice (in the 2,3-, 2,4-, 2,5-, 2,6-, 3,4- or 3,5-positions), three times (in the 2,3,4-, 2,3,5-, 2,3,6-, 2,4,5-, 2,4,6- or 3,4,5-positions) or, in case (a), also four times (in the 2,3,4,5-, 2,3,4,6- or 2,3,5,6 positions). Preferred as the radical Ar are 2,4-disubstituted and o- or p-monosubstituted phenyl groups.

Alkyl (and the alkyl portion of alkoxy) is preferably unbranched, has preferably 1-4, particularly 1-3, C-atoms and is preferably methyl, and also ethyl, propyl, isopropyl, butyl, isobutyl, sec-butyl, tert-butyl, pentyl or isopentyl.

Alkenyl is preferably unbranched, has in particular 2-4, preferably 3, C-atoms and is preferably allyl, and also vinyl, prop-1-en-1-yl, butenyl, such as but-1-en-1-yl, but-2-en-1-yl, but-3-en-1-yl, pentenyl, such as pent-1-en-1-yl, pent-2-en-1-yl or pent-3-en-1-yl. The alkenyl groups can, however, also be branched; examples include 1-methylprop-2-en-1-yl, 1-methylbut-2-en-1yl, 2-methylbut-3-en-1-yl and 1,1-dimethylprop-2-en-1-yl.

Preferred alkynyl groups are unbranched and have, in particular, 3, but also 2,4 or 5, C-atoms, such as propargyl (=prop-2-yn-1-yl), and also ethynyl, prop-1-yn-1-yl, butynyl, such as but-1-yn-1-yl, but-2-yn-1-yl, but-3-yn-1-yl, pentynyl, such as pent-1-yn-1-yl, pent-2-yn-1-yl or pent-3-yn-1-yl. The alkynyl groups can, however, also be branched; examples include 1-methyl-prop-2-yn-1-yl, 1-methylbut-2-yn-1-yl, 2-methylbut-3-yn-1-yl and 1,1-dimethylprop-2-yn-1-yl.

Hydroxyalkyl is preferably unbranched, has, in particular, 2-4, preferably 2 or 3, C-atoms and is preferably 2-hydroxyethyl or 3-hydroxypropyl, and also, for example, hydroxymethyl, 1-hydroxyethyl, 1- or 2-hydroxy-propyl, 1- or 2-hydroxy-1-methylethyl, 1-, 2-, 3- or 4-hydroxybutyl or 1-, 2-, 3-, 4- or 5-hydroxypentyl.

Preferred alkyloxycarbonylmethyl groups have 1-4, in particular 1-3, C atoms in the alkyloxy radical, such as methoxy- and ethoxy-carbonylmethyl, and also propoxy-, isopropoxy-, butoxy-, isobutoxy-, sec-butoxy-, tert-butoxy-, pentoxy- and isopentoxycarbonylmethyl.

In compounds of formula Ib, the following substituents on the phenyl radical are, for example, particularly preferred: hydroxyl (only if at least one other substituent is present on the phenyl radical which is different from hydroxyl), methoxy (only if at least one other substituent is present on the phenyl radical which is different from methoxy), ethoxy, propoxy, isopropoxy, butoxy, vinyloxy, allyloxy, propargyloxy, 2-hydroxyethoxy, cyanomethoxy, carboxymethoxy, methoxycarbonylmethoxy, ethoxycarbonylmethoxy, methylthio, ethylthio, propylthio, isopropylthio, butylthio, vinylthio, allylthio, propargylthio, 2-hydroxyethylthio, cyanomethylthio, carboxymethylthio, methoxycarbonylmethylthio, ethoxycarbonylmethylthio, methylsulfinyl, ethylsulfinyl, propylsulfinyl, isopropylsulfinyl, butylsulfinyl, vinylsulfinyl, allylsulfinyl, propargylsulfinyl, 2-hydroxyethylsulfinyl, cyanomethylsulfinyl, carboxymethylsulfinyl, methoxycarbonylmethylsulfinyl or ethoxycarbonylmethylsulfinyl.

The invention particularly relates to those compounds of formula I in which at least one of the radicals mentioned has one of the preferred meanings mentioned in the foregoing text. Some preferred groups of compounds can be expressed by the following partial formulae Ic to Is, which correspond to the formula I and wherein the radical Ar is a phenyl radical which is substituted as follows:

(a) in the case where —A=B—=—CH=N—:
in Ic: by an alkynyloxy, cyanomethoxy, carboxymethoxy or alkyloxycarbonylmethoxy group and optionally by one or two additional hydroxyl, alkyloxy, alkenyloxy and/or alkynyloxy groups, the alkyl alkenyl and alkynyl groups each having up to 4 C atoms;

in Id: by an alkynyloxy, cyanomethoxy, carboxymethoxy or alkyloxycarbonylmethoxy group and optionally by one or two additional hydroxyl, alkyloxy, alkenyloxy and/or alkynyloxy groups, the alkyl, alkenyl and alkynyl groups each having up to 3 C atoms:

in Ie: by a propargyloxy, cyanomethoxy, carboxymethoxy or alkyloxycarbonylmethoxy group and optionally by one or two additional alkyloxy groups or by an additional allyloxy or propargyloxy group, the alkyloxy groups each having 1-3 C atoms;

in If: by a propargyloxy group and optionally additionally by one or two methoxy groups;

in Ig: by a cyanomethoxy group and optionally additionally by one or two methoxy groups;

in Ih: by a carboxymethoxy group and optionally additionally by one or two methoxy groups;

in Ii: by a methoxycarbonylmethoxy or ethoxycarbonylmethoxy group and optionally additionally by one or two methoxy groups.

(b) In the case where —A=B—=—N=CH—:
in Ij: by one or two hydroxyl and/or Z-R groups;

in Ik: by an alkenyloxy, alkynyloxy, cyanomethoxy, carboxymethoxy, alkyloxycarbonylmethoxy, alkylthio or alkylsulfinyl group and optionally by an additional hydroxyl, alkyloxy, alkenyloxy or alkynyloxy group, the alkyl, alkenyl and alkynyl groups each having up to 3 C atoms;

in Il: by an ethoxy, propyloxy, isopropyloxy, allyloxy, propargyloxy, 2-hydroxyethoxy, cyanomethoxy, carboxymethoxy, alkyloxycarbonylmethoxy, methylthio or methylsulfinyl group and optionally by an additional hydroxyl, alkyloxy, allyloxy or propargyloxy group, the alkyloxy groups having in each case 1-3 C atoms.

in Im: by one or two allyloxy, allylthio, propargyloxy and/or propargylthio groups and optionally additionally by an alkyloxy or alkylthio group with 1-3 C atoms in each case;

in In: by an allyloxy or allylthio group and optionally additionally by a methoxy group;

in Io: by a propargyloxy or propargylthio group and optionally additionally by a methoxy group;

in Ip: by a cyanomethoxy or cyanomethylthio group and optionally additionally by a methoxy group;

in Iq: by a carboxymethoxy or carboxymethylthio group and optionally additionally by a methoxy group;

in Ir: by a methoxycarbonylmethoxy, ethoxycarbonylmethoxy, methoxycarbonylmethylthio or ethoxycarbonylmethylthio group and optionally additionally by a methoxy group;

in Is: by an alkylthio, alkenylthio or alkynylthio group having up to 3 C atoms in each case.

Those compounds of the formulae I or Ia to Is in which the subsituents are in the 2- and/or 4-position are particularly preferred.

The invention further relates to a process for the preparation of the compounds of formula I and their physiologically acceptable salts, wherein a diaminopyridine of formula II

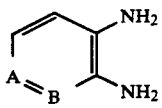   II wherein
the group —A═B— is as defined above, is reacted with a benzoic acid of formula III

   III wherein
Ar is as defined above, or with one of its reactive derivatives or with an aldehyde of formula IV

   IV wherein
Ar is as defined above, in the presence of an oxidizing agent; or
a compound which corresponds to formula I, but which contains one or more free hydroxyl groups instead of one or more ether groups, is treated with an etherifying agent, or
a compound which corresponds to formula I, but which contains one or more protected hydroxyl or mercapto groups instead of one or more free hydroxyl and/or mercapto groups, is treated with a solvolysing or hydrogenolysing agent,
and, where appropriate, hydroxyl groups in the product obtained are etherified and/or mercapto groups are converted into thioether groups and/or thioether groups are oxidized to sulfinyl groups and/or ester and/or cyano groups are hydrolysed and/or carboxyl groups are esterified and/or a compound obtained is converted into one of its physiologically acceptable salts by treatment with an acid or base.

The compounds of formula I are otherwise prepared be methods known in themselves, as described in the literature (for example in the standard works, such as Houben-Weyl, Methoden der Organischen Chemie (Methods of Organic Chemistry), Georg-Thieme-Verlag, Stuttgart, but in particular in German Offenlegungsschrift 2,305,339, all of whose disclosures are incorporated by reference herein), under reaction conditions which are known and suitable for the reactions mentioned. In these preparations, variants which are known in themselves but which are not mentioned here in more detail, can also be used.

When desired, the starting materials can also be formed in situ, in such a way that they are not isolated from the reaction mixture but are immediately reacted further to produce the compounds of formula I. On the other hand, it is also possible to carry out the reaction in steps, it being possible for further intermediate products to be isolated.

Preferably, the compounds of formula I are obtained by reaction of II with benzoic acids of formula III or their reactive derivatives. Suitable reactive derivatives include, in particular, the corresponding nitriles, acid halides, esters, amides, imidates, thioimidates, imidic acid halides, amidines, thiocarboxylates, dithiocarboxylates or ortho esters.

Some of the starting materials II and III are known. If they are not known, they can be prepared by methods which are known in themselves. Thus, many benzoic acids of formula III can be obtained, for example, by etherification of corresponding hydroxy-, dihydroxy- or trihydroxy-benzoic acids; this etherification can also be carried out in steps.

Specifically, the reaction of II with III can be carried out in the presence or absence of an inert solvent at temperatures of −20° to about 250° C., preferably 60° to 150° C. Suitable solvents include, for example, hydrocarbons such as benzene, toluene, xylenes or mesitylene; tertiary bases such as triethylamine, pyridine or picolines; glycols and glycol ethers, such as ethylene glycol, diethylene glycol or 2-methoxy-ethanol; ketones such as acetone; ethers such as tetrahydrofuran or dioxane; amides such as dimethylformamide; or sulfoxides such as dimethyl sulfoxide. Mixtures of these solvents are also suitable. In some cases, the addition of catalytic amounts of an acid, such as p-toluenesulfonic acid or the addition of a dehydrating agent, such as phosphorus oxychloride, polyphosphoric acid or thionyl chloride is recommended, it being possible for the dehydrating agent also to serve as the solvent.

If the free benzoic acids of formula III are used, the reaction is preferably carried out in the presence of one of the mentioned dehydrating agents and, if appropriate, a tertiary base, such as pyridine or triethylamine, preferably at temperatures of −20° to 150°.

The reaction can also be carried out in steps. Thus, it is possible, for example, partially to acylate II with an acid chloride of the formula Ar-COCl to give the 2-amino-3-ArCONH-pyridine, 3-amino-4-ArCONH-pyridine or to give the 4-amino-3-ArCONH-pyridine (or to give a mixture of the two latter isomers), which then is dehydrated to I, for example, with POCl$_3$.

It is also possible to use, instead of III, a corresponding aldehyde of formula IV, if, at the same time, the reaction is carried out in the presence of an oxidizing agent. The oxidizing agent preferably used is sulfur in a hydrocarbon, such as benzene, toluene, xylene or mesitylene or sodium disulfite in solvents such as dimethylacetamide, in each case at temperatures of about 80° to about 200°. This reaction variant is particularly suitable for the preparation of compounds of formula I which contain groups (for example alkyloxycarbonyl groups) which are not completely inert towards certain dehydrating agents (for example POCl$_3$). The aldehydes of formula IV are, generally speaking, new and can be obtained, for example, by etherification of the corresponding hydroxyaldehydes.

The compounds of formula I, in particular those of formula Ia, can also be obtained by etherifying a compound which otherwise corresponds to formula I, but which contains one (or more) free hydroxyl group(s) instead of one (or more) ether groups.

Suitable starting materials for this etherification correspond, for example, to general formula V

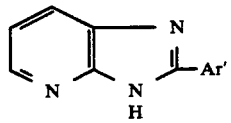   V wherein
Ar' is phenyl which is substituted by a hydroxyl group and can additionally be substituted by one to three alkynyloxy groups and/or one or two cyanomethoxy, carboxymethoxy, alkyloxycarbonylmethoxy, hydroxyl; alkyloxy and/or alkenyloxy groups, but is substituted a maximum of four times. Etherification agents are preferably those of the formula VI

X—R wherein
X is Cl, Br, I, OH, alkylsulfonyloxy or arylsulfonyloxy and;
R is alkynyl, cyanomethyl, carboxymethyl, alkyloxycarbonylmethyl, alkyl or alkenyl,
the alkyl, alkenyl and alkynyl groups each having up to 5, and the aryl groups 6–10 C-atoms.

Typical etherification agents include, for example, propargyl chloride or bromide, chloro-or bromoacetonitrile, chloro- or bromoacetic acid and their methyl and ethyl esters, methyl, ethyl, propyl, isopropyl and allyl chloride or bromide.

For the etherification, the hydroxy compound V is preferably initially converted into one of its salts, for example, the Na salt, which then is reacted with VI in one of the solvents indicated at temperatures of about 0° to about 120°. It is also possible to etherify the free hydroxy compoond V with the appropriate alcohol VI (X=OH) in the presence of diethyl azodicarboxylate/triphenylphosphine, preferably in a solvent, such as tetrahydrofuran or dioxane at temperatures of about 10° to about 40°.

Compounds of formula I, in particular those of formula Ib, which contain free hydroxyl and/or mercapto groups, can also be obtained by solvolysis or hydrogenolysis of corresponding compounds in which the hydroxyl and/or mercapto groups are blocked by protective groups which can be split off in this manner.

The starting materials for this solvolysis or hydrogenolysis correspond to formula VII

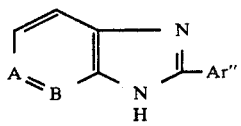

VII wherein
Ar" is phenyl which
in the case (a) (—A=B—=—CH=N—) is substituted by one or two protected hydroxyl groups and by one or two alkynyloxy, cyanomethoxy, carboxymethoxy, and/or alkyloxycarbonylmethoxy groups and can be substituted by one additional hydroxyl, alkyloxy, alkenyloxy or alkynyloxy group, but is substituted a maximum of four times, or which
in the case (b) (—A=B—=N=CH—) is substituted by one to three protected hydroxyl and/or mercapto groups and can additionally carry one or two free hydroxyl and/or mercapto and/or Z-R groups (Z and R being as defined above), but overall is substituted a maximum of three times, but wherein the phenyl radical is only substituted by protected hydroxyl or by methoxy groups if it carries at the same time at least one other substituent differing from these The starting materials of formula VII can be obtained, for example, by reaction of II with benzoic acids of the formula HOOC—Ar" or their reactive derivatives by the above mentioned methods.

Suitable protective groups are the known hydroxyl protective groups and mercapto protective groups. These expressions relate to groups which are suitable to protect hydroxyl and mercapto groups from chemical reactions, but which are easily removable after the desired chemical reaction at another site in the molecule has been carried out. Examples of typical protective groups are easily cleavable ester, thioester, ether and thioether groups with preferably 1–12 C atoms, specifically, for example, alkanoyl having preferably 1–6 C atoms, such as acetyl, aroyl having preferably 7–11 C atoms, such as benzoyl, unsubstituted and substituted aryl and aralkyl each having up to 11 C atoms, such as 2,4-dinitrophenyl, benzyl, triphenylmethyl and also, for example, tetrahydropyranyl. The nature and size of the protective groups are not critical, since thay are split off according to the present process.

Solvolysis of the protective groups is preferably carried out in the form of hydrolysis in aqueous or aqueou-salcoholic medium in the presence of acids, such as hydrochloric acid, or of bases, such as sodium hydroxide or potassium hydroxide, at temperatures of about 0° to 100°.

Hydrogenolysis of the protective groups which are split off by hydrogenolysis is carried out, for example, in the presence of a heavy metal catalyst, such as platinum, palladium or nickel in an inert solvent, such as methanol, ethanol, tetrahydrofuran or ethyl acetate at temperatures of about 0° to 100° and pressures of about 1 to 200 bar.

If desired, one or more hydroxyl groups present in the product obtained can be etherified and/or mercapto group(s) can be converted into thioether groups.

Suitable etherification agents (or thioetherification agents) are preferably those of the formula X-R (VI), in which X and R have the above-mentioned meanings but in which R can also denote hydroxyalkyl having up to 5 C atoms.

Typical etherification agents (or thioetherification agents) are, for example, those particularized above and, in addition, 2-hydroxyethyl chloride or bromide.

The etherification (or thioetherification) is preferably carried out under the conditions given above for the etherification of V.

In addition, if desired, a thioether group optionally present in an obtained product of formula I can be oxidized to a sulfinyl group, preferably with hydrogen peroxide, peracids or Cr(VI) compounds, such as chromic acid, in the presence of an inert solvent, such as water, an alcohol (for example methanol or ethanol), an acid (for example, acetic acid) or a ketone (for example acetone) at temperatures of about −20° to 100°.

Furthermore, an ester or cyanide group present in an obtained product of formula I can be hydrolysed in a manner known in itself to a carboxyl group, for example with aqueous or alcoholic KOH or NaOH at temperatures of about 20° to 100° and/or a carboxyl group present in an obtained product of formula I can be esterified, for example, with the appropriate alcohol, such as methanol or ethanol, in the presence of an acid, such as HCl, H$_2$SO$_4$ or p-toluenesulfonic acid at temperatures of about 20° to 100°.

A base of formula I can be converted into an acid addition salt with an acid. Suitable acids for this conversion are those which provide physiologically acceptable salts. Thus, inorganic acids can be used, for example, sulfuric acid, nitric acid, hydrohalic acids, such as hydrochloric acid or hydrobromic acid, phosphoric acids, such as orthophosphoric acid, sulfamic acids, and also organic acids, in particular aliphatic, alicyclic, araliphatic, aromatic or heterocyclic monobasic or multibasic carboxlic, sulfonic or sulfuric acids, for example, formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methanesulfonic or ethanesulfonic acid, ethanedisulfonic acid, 2-hydroxyethanesulfonic acid, benzenesulfonic acid, p-toluenesulfonic acid, naphthalenemonosulfonic and naphthalenedisulfonic acids and lauryl sulfuric acid.

An acid of formula I can be converted into one of its physiologically acceptable metal or ammonium salts by reaction with a base. Particularly suitable salts are the sodium, potassium, magnesium, calcium and ammonium salts, and also substituted ammonium salts, for example, the dimethylammonium, diethylammonium or diisopropylammonium, the monoethanolammonium, diethanolammonium and triethanolammonium, cyclohexylammonium, dicyclohexylammonium and dibenzylethylenediammonium salts.

The invention also relates to the use of the compounds of formula I and their physiologically acceptable salts for the preparation of pharmaceutical formulations, in particular by non-chemical means. For this purpose, they can be converted into a form suitable for administration together with at least one solid, liquid and/or semi-liquid vehicle or auxiliary and, if appropriate, in combination with one or more additional active ingredients.

The invention also relates to agents, in particular pharmaceutical formulations, containing at least one compound of formula I and/or one of its physiologically acceptable salts.

These formulations can be used as medicaments in human or veterinary medicine. Suitable vehicles include organic or inorganic substances which are suitable for enteral (for example oral), parenteral or topical administration and which do not react with the new compounds, for example water, vegetable oils, benzyl alcohols, polyethylene glycols, glyceryl triacetate, gelatin, carbohydrates, such as lactose or starch, magnesium stearate, talc and vaseline. Particularly suitable for oral use are tablets, coated tablets, capsules, syrups, juices or drops, for rectal use, suppositories, for parenteral use, solutions, preferably oily or aqueous solutions, and also suspensions, emulsions or implants, for topical use, ointments, creams or powder. The new compounds can also be lyophilized and the lyophilizates obtained can be used, for example, for the preparation of products for injection. The formulations mentioned can be sterilized and/or contain auxiliaries, such as lubricants, preservatives, stabilizers and/or wetting agents, emulsifiers, salts to alter the osmotic pressure, buffer substances, dyes, flavorings and/or aromatics. If desired, they can also contain one or more other active ingredients, for example one or more vitamins.

The invention also relates to the use of the compounds of formula I for combating diseases, in particular cardiac insufficiency, and their use for the therapeutic treatment of the human or animal body.

For this purpose, the substances according to the invention are, as a rule, administered in analogy to known substances with positive inotropic activity, such as Sulmazol or Amrinon, preferably in doses of about 10 to 500 mg, in particular 20 to 100 mg, per unit dose. The daily dose is preferably about 0.2 to 10 mg/kg of body weight. However, conventionally, the particular dose for each patient depends on a wide range of factors, for example on the effectiveness of the particular compound employed, on the age, weight, general state of health, sex, and diet of the patient, on the time and mode of administration, on the rate of elimination, combination with other medicaments and severity of the particular disease to which the therapy is applied. Oral administration is preferred. In comparison to the digitalis glycosides hitherto used for the therapy of cardiac insufficiency, the compounds of formula I are distinguished by an improved therapeutic range and peripheral relief.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

In the following examples, "usual work-up" indicates: If necessary, water or dilute sodium hydroxide solution is added; extraction is carried out with an organic solvent, such as ethyl acetate, chloroform or dichloromethane; the organic phase is separated off, dried over sodium sulfate, filtered and concentrated; and purification is by chromatography and/or crystallization.

In the foregoing and subsequent text, all temperatures are quoted in degrees centigrade.

EXAMPLE 1

A mixture of 10.9 g of 2,3-diaminopyridine (IIa) and 20.6 g of 2-methoxy-4-propargyloxybenzoic acid (m.p. 142°; obtainable by the reaction of methyl 2,4-dihydroxybenzoate with propargyl chloride to give methyl 2-hydroxy-4-propargyloxybenzoate (m.p. 100°); reaction of this with methyl iodide to give methyl 2-methoxy-4-propargyloxybenzoate (m.p. 88°) and hydrolysis) is added in portions with stirring to 500 ml of $POCl_3$. The mixture is boiled for 4 hours, concentrated, and the residue is treated with 375 ml of 10% hydrochloric acid. The precipitated 2-(2-methoxy-4-propargyloxyphenyl)imidazo (4,5-b) pyridine hydrochloride ("M") is filtered off. M.p. 247° (from methanol).

Analogously, the following compounds are obtained from IIa or from 3,4 diaminopyridine (IIb) and the appropriate benzoic acids of formula III (for example, o-propargyloxybenzoic acid, m.p. 82°; m-propargyloxybenzoic acid, m.p. 130°; p-propargyloxybenzoic acid, m.p. 224°; 2-methoxy-5-propargyloxybenzoic acid, m.p. 103°; 3-methoxy-4-propargyloxybenzoic acid, m.p. 195°; 3,5-dimethoxy-4-propargyloxybenzoic acid, m.p. 208°; 2,4-bispropargyloxybenzoic acid, m.p. 152°), it being possible for the reaction temperature to be kept between 70° and 110°:

2-(p-Ethinyloxyphenyl)imidazo(4,5-b)pyridine.
2-(o-Propargyloxyphenyl)imidazo(4,5-b)pyridine, hydrochloride, m.p. 223°.
2-(m-Propargyloxyphenyl)imidazo(4,5-b)pyridine, hydrochloride, m.p. 195°.
2-(p-Propargyloxyphenyl)imidazo(4,5-b)pyridine, m.p. 218°.

2-(p-Pent-3-in-1-yloxyphenyl)imidazo(4,5-b)pyridine.
2-(o-Cyanomethoxyphenyl)imidazo(4,5-b)pyridine.
2-(m-Cyanomethoxyphenyl)imidazo(4,5-b)pyridine.
2-(p-Cyanomethoxyphenyl)imidazo(4,5-b)pyridine.
2-(o-Carboxymethoxyphenyl)imidazo(4,5-b)pyridine.
2-(m-Carboxymethoxyphenyl)imidazo(4,5-b)pyridine.
2-(p-Carboxymethoxyphenyl)imidazo(4,5-b)pyridine.
2-(o-Methoxycarbonylmethoxyphenyl)imidazo(4,5-b)pyridine.
2-(m-Methoxycarbonylmethoxyphenyl)imidazo(4,5-b)pyridine.
2-(p-Methoxycarbonylmethoxyphenyl)imidazo(4,5-b)pyridine.
2-(o-Ethoxycarbonylmethoxyphenyl)imidazo(4,5-b)pyridine.
2-(m-Ethoxycarbonylmethoxyphenyl)imidazo(4,5-b)pyridine.
2-(p-Ethoxycarbonylmethoxyphenyl)imidazo(4,5-b)pyridine, hemifumarate, m.p. 158°.
2-(p-Propyloxycarbonylmethoxyphenyl)imidazo(4,5-b)pyridine.
2-(p-Butyloxycarbonylmethoxyphenyl)imidazo(4,5-b)pyridine.
2-(p-Pentyloxycarbonylmethoxyphenyl)imidazo(4,5-b)pyridine.
2-(2-Hydroxy-4-propargyloxyphenyl)imidazo(4,5-b)pyridine.
2-(3-Hydroxy-4-propargyloxyphenyl)imidazo(4,5-b)pyridine.
2-(4-Hydroxy-2-propargyloxyphenyl)imidazo(4,5-b)pyridine.
2-(2-Methoxy-3-propargyloxyphenyl)imidazo(4,5-b)pyridine.
2-(2-Methoxy-5-propargyloxyphenyl)imidazo(4,5-b)pyridine, hydrochloride, m.p. 262°.
2-(2-Methoxy-6-propargyloxyphenyl)imidazo(4,5-b)pyridine.
2-(3-Methoxy-2-propargyloxyphenyl)imidazo(4,5-b)pyridine.
2-(3-Methoxy-4-propargyloxyphenyl)imidazo(4,5-b)pyridine, hydrochloride, m.p. 238°.
2-(3-Methoxy-5-propargyloxyphenyl)imidazo(4,5-b)pyridine.
2-(3-Methoxy-6-propargyloxyphenyl)imidazo(4,5-b)pyridine.
2-(4-Methoxy-2-propargyloxyphenyl)imidazo(4,5-b)pyridine, fumarate, m.p. 220°.
2-(4-Methoxy-3-propargyloxyphenyl)imidazo(4,5-b)pyridine.
2-(2-Ethoxy-3-propargyloxyphenyl)imidazo(4,5-b)pyridine.
2-(2-Ethoxy-4-propargyloxyphenyl)imidazo(4,5-b)pyridine.
2-(2-Ethoxy-5-propargyloxyphenyl)imidazo(4,5-b)pyridine.
2-(2-Ethoxy-6-propergyloxyphenyl)imidazo(4,5-b)pyridine.
2-(3-Ethoxy-2-propargyloxyphenyl)imidazo(4,5-b)pyridine.
2-(3-Ethoxy-4-propargyloxyphenyl)imidazo(4,5-b)pyridine.
2-(3-Ethoxy-5-propargyloxyphenyl)imidazo(4,5-b)pyridine.
2-(4-Ethoxy-2-propargyloxyphenyl)imidazo(4,5-b)pyridine.
2-(4-Ethoxy-3-propargyloxyphenyl)imidazo(4,5-b)pyridine.
2-(3,5-Dimethoxy-4-propargyloxyphenyl)imidazo(4,5-b)pyridine, hydrochloride, m.p. 250°.
2-(3,5-Diethoxy-4-propargyloxyphenyl)imidazo(4,5-b)pyridine.
2-(2-Allyloxy-4-propargyloxyphenyl)imidazo(4,5-b)pyridine.
2-(3-Allyloxy-4-propargyloxyphenyl)imidazo(4,5-b)pyridine.
2-(4-Allyloxy-2-propargyloxyphenyl)imidazo(4,5-b)pyridine.
2-(2,4-Bis-propargyloxyphenyl)imidazo(4,5-b)pyridine, hemifumarate, m.p. 210°.
2-(4-Cyanomethoxy-2-hydroxyphenyl)imidazo(4,5-b)pyridine.
2-(4-Cyanomethoxy-2-methoxyphenyl)imidazo(4,5-b)pyridine, hemifumarate, m.p. 212°.
2-(4-Cyanomethoxy-2-ethoxyphenyl)imidazo(4,5-b)pyridine.
2-(2-Allyloxy-4-cyanomethoxyphenyl)imidazo(4,5-b)pyridine.
2-(2,4-Bis-cyanomethoxyphenyl)imidazo(4,5-b)pyridine.
2-(2-Cyanomethoxy-4-propargyloxyphenyl)imidazo(4,5-b)pyridine.
2-(4-Cyanomethoxy-2-propargyloxyphenyl)imidazo(4,5-b)pyridine.
2-(4-Carboxymethoxy-2-hydroxyphenyl)imidazo(4,5-b)pyridine.
2-(4-Carboxymethoxy-2-methoxyphenyl)imidazo(4,5-b)pyridine, m.p. 235°, hydrochloride, m.p. 262°
2-(4-Carboxymethoxy-2-ethoxyphenyl)imidazo(4,5-b)pyridine.
2-(2-Allyloxy-4-carboxymethoxyphenyl)imidazo(4,5-b)pyridine.
2-(2,4-Bis-carboxymethoxyphenyl)imidazo(4,5-b)pyridine.
2-(2-Carboxymethoxy-4-propargyloxyphenyl)imidazo(4,5-b)pyridine.
2-(4-Carboxymethoxy-2-propargyloxyphenyl)imidazo(4,5-b)pyridine.
2-(4-Methoxycarbonylmethoxy-2-hydroxyphenyl)imidazo(4,5-b)pyridine.
2-(4-Methoxycarbonylmethoxy-2-methoxyphenyl)imidazo(4,5-b)pyridine.
2-(2-Ethoxy-4-methoxycarbonylmethoxyphenyl)imidazo(4,5-b)pyridine.
2-(2-Allyloxy-4-methoxycarbonylmethoxyphenyl)imidazo(4,5-b)pyridine.
2-(2,4-Bis-methoxycarbonylmethoxyphenyl)imidazo(4,5-b)pyridine.
2-(2-Methoxycarbonylmethoxy-4-propargyloxyphenyl)imidazo(4,5-b)pyridine.
2-(4-Methoxycarbonylmethoxy-2-propargyloxyphenyl)imidazo(4,5-b)pyridine.
2-(4-Ethoxycarbonylmethoxy-2-hydroxyphenyl)imidazo(4,5-b)pyridine.
2-(4-Ethoxycarbonylmethoxy-2-methoxyphenyl)imidazo(4,5-b)pyridine, hemifumarate, m.p. 198°.
2-(2-Ethoxy-4-ethoxycarbonylmethoxyphenyl)imidazo(4,5-b)pyridine.
2-(2-Allyloxy-4-ethoxycarbonylmethoxyphenyl)imidazo(4,5-b)pyridine.
2-(2,4-Bis-ethoxycarbonylmethoxyphenyl)imidazo(4,5-b)pyridine.
2-(2-Ethoxycarbonylmethoxy-4-propargyloxyphenyl)imidazo(4,5-b)pyridine.
2-(4-Ethoxycarbonylmethoxy-2-propargyloxyphenyl)imidazo(4,5-b)pyridine.

2-(o-Ethoxyphenyl)imidazo(4,5-c)pyridine.
2-(m-Ethoxyphenyl)imidazo(4,5-c)pyridine.
2-(p-Ethoxyphenyl)imidazo(4,5-c)pyridine.
2-(o-Propyloxyphenyl)imidazo(4,5-c)pyridine.
2-(m-Propyloxyphenyl)imidazo(4,5-c)pyridine.
2-(p-Propyloxyphenyl)imidazo(4,5-c)pyridine.
2-(o-Isopropyloxyphenyl)imidazo(4,5-c)pyridine.
2-(m-Isopropyloxyphenyl)imidazo(4,5-c)pyridine.
2-(p-Isopropyloxyphenyl)imidazo(4,5-c)pyridine.
2-(o-Allyloxyphenyl)imidazo(4,5-c)pyridine, hydrochloride, m.p. 212°.
2-(m-Allyloxyphenyl)imidazo(4,5-c)pyridine.
2-(p-Allyloxyphenyl)imidazo(4,5-c)pyridine, fumarate, m.p. 215°.
2-(p-Ethinyloxyphenyl)imidazo(4,5-c)pyridine.
2-(o-Propargyloxyphenyl)imidazo(4,5-c)pyridine, fumarate, m.p. 192°.
2-(m-Propargyloxyphenyl)imidazo(4,5-c)pyridine. hydrochloride, m.p. 250°.
2-(p-Propargyloxyphenyl)imidazo(4,5-c)pyridine, hemifumarate, m.p. 230°.
2-(p-Pent-3-in-1-yloxyphenyl)imidazo(4,5-c)pyridine.
2-(o-2-Hydroxyethoxyphenyl)imidazo(4,5-c)pyridine.
2-(m-2-Hydroxyethoxyphenyl)imidazo(4,5-c)pyridine.
2-(p-2-Hydroxyethoxyphenyl)imidazo(4,5-c)pyridine.
2-(o-Cyanomethoxyphenyl)imidazo(4,5-c)pyridine.
2-(m-Cyanomethoxyphenyl)imidazo(4,5-c)pyridine.
2-(p-Cyanomethoxyphenyl)imidazo(4,5-c)pyridine.
2-(o-Carboxymethoxyphenyl)imidazo(4,5-c)pyridine.
2-(m-Carboxymethoxyphenyl)imidazo(4,5-c)pyridine.
2-(p-Carboxymethoxyphenyl)imidazo(4,5-c)pyridine.
2-(o-Methoxycarbonylmethoxyphenyl)imidazo(4,5-c)pyridine.
2-(m-Methoxycarbonylmethoxyphenyl)imidazo(4,5-c)pyridine.
2-(p-Methoxycarbonylmethoxyphenyl)imidazo(4,5-c)pyridine.
2-(o-Ethoxycarbonylmethoxyphenyl)imidazo(4,5-c)pyridine.
2-(m-Ethoxycarbonylmethoxyphenyl)imidazo(4,5-c)pyridine.
2-(p-Ethoxycarbonylmethoxyphenyl)imidazo(4,5-c)pyridine.
2-(p-Propyloxycarbonylmethoxyphenyl)imidazo(4,5-c)pyridine.
2-(p-Butyloxycarbonylmethoxyphenyl)imidazo(4,5-c)pyridine.
2-(p-Pentyloxycarbonylmethoxyphenyl)imidazo(4,5-c)pyridine.
2-(p-Mercaptophenyl)imidazo(4,5-c)pyridine.
2-(o-Methylthiophenyl)imidazo(4,5-c)pyridine, hydrochloride, m.p. 230°.
2-(m-Methylthiophenyl)imidazo(4,5-c)pyridine.
2-(o-Methylthiophenyl)imidazo(4,5-c)pyridine.
2-(o-Ethylthiophenyl)imidazo(4,5-c)pyridine.
2-(m-Ethylthiophenyl)imidazo(4,5-c)pyridine.
2-(p-Ethylthiophenyl)imidazo(4,5-c)pyridine.
2-(o-Propylthiophenyl)imidazo(4,5-c)pyridine.
2-(m-Propylthiophenyl)imidazo(4,5-c)pyridine.
2-(p-Propylthiophenyl)imidazo(4,5-c)pyridine.
2-(o-Allylthiophenyl)imidazo(4,5-c)pyridine.
2-(m-Allylthiophenyl)imidazo(4,5-c)pyridine.
2-(p-Allylthiophenyl)imidazo(4,5-c)pyridine.
2-(o-Propargylthiophenyl)imidazo(4,5-c)pyridine. m.p. 248°.
2-(m-Propargylthiophenyl)imidazo(4,5-c)pyridine.
2-(p-Propargylthiophenyl)imidazo(4,5-c)pyridine.
2-(o-2-Hydroxyethylthiophenyl)imidazo(4,5-c)pyridine.
2-(m-2-Hydroxyethylthiophenyl)imidazo(4,5-c)pyridine.
2-(p-2-Hydroxyethylthiophenyl)imidazo(4,5-c)pyridine.
2-(o-Cyanomethylthiophenyl)imidazo(4,5-c)pyridine.
2-(m-Cyanomethylthiophenyl)imidazo(4,5-c)pyridine.
2-(p-Cyanomethylthiophenyl)imidazo(4,5-c)pyridine.
2-(o-Carboxymethylthiophenyl)imidazo(4,5-c)pyridine.
2-(m-Carboxymethylthiophenyl)imidazo(4,5-c)pyridine.
2-(p-Carboxymethylthiophenyl)imidazo(4,5-c)pyridine.
2-(o-Methoxycarbonylmethylthiophenyl)imidazo(4,5-c)pyridine.
2-(m-Methoxycarbonylmethylthiophenyl)imidazo(4,5-c)pyridine.
2-(p-Methoxycarbonylmethylthiophenyl)imidazo(4,5-c)pyridine.
2-(o-Ethoxycarbonylmethylthiophenyl)imidazo(4,5-c)pyridine.
2-(m-Ethoxycarbonylmethylthiophenyl)imidazo(4,5-c)pyridine.
2-(p-Ethoxycarbonylmethylthiophenyl)imidazo(4,5-c)pyridine.
2-(o-Methylsulfinylphenyl)imidazo(4,5-c)pyridine, hydrochloride, m.p. 230°.
2-(m-Methylsulfinylphenyl)imidazo(4,5-c)pyridine.
2-(p-Methylsulfinylphenyl)imidazo(4,5-c)pyridine.
2-(o-Ethylsulfinylphenyl)imidazo(4,5-c)pyridine.
2-(m-Ethylsulfinylphenyl)imidazo(4,5-c)pyridine.
2-(p-Ethylsulfinylphenyl)imidazo(4,5-c)pyridine.
2-(o-Propylsulfinylphenyl)imidazo(4,5-c)pyridine.
2-(m-Propylsulfinylphenyl)imidazo(4,5-c)pyridine.
2-(p-Propylsulfinylphenyl)imidazo(4,5-c)pyridine.
2-(o-Allylsulfinylphenyl)imidazo(4,5-c)pyridine.
2-(m-Allylsulfinylphenyl)imidazo(4,5-c)pyridine.
2-(p-Allylsulfinylphenyl)imidazo(4,5-c)pyridine.
2-(o-Propargylsulfinylphenyl)imidazo(4,5-c)pyridine.
2-(m-Propargylsulfinylphenyl)imidazo(4,5-c)pyridine.
2-(p-Propargylsulfinylphenyl)imidazo(4,5-c)pyridine.
2-(o-2-Hydroxyethylsulfinylphenyl)imidazo(4,5-c)pyridine.
2-(m-2-Hydroxyethylsulfinylphenyl)imidazo(4,5-c)pyridine.
2-(p-2-Hydroxyethylsulfinylphenyl)imidazo(4,5-c)pyridine.
2-(o-Cyanomethylsulfinylphenyl)imidazo(4,5-c)pyridine.
2-(m-Cyanomethylsulfinylphenyl)imidazo(4,5-c)pyridine.
2-(p-Cyanomethylsulfinylphenyl)imidazo(4,5-c)pyridine.
2-(o-Carboxymethylsulfinylphenyl)imidazo(4,5-c)pyridine.
2-(m-Carboxymethylsulfinylphenyl)imidazo(4,5-c)pyridine.
2-(p-Carboxymethylsulfinylphenyl)imidazo(4,5-c)pyridine.
2-(o-Methoxycarbonylmethylsulfinylphenyl)imidazo(4,5-c)pyridine.
2-(m-Methoxycarbonylmethylsulfinylphenyl)imidazo(4,5-c)pyridine.
2-(p-Methoxycarbonylmethylsulfinylphenyl)imidazo(4,5-c)pyridine.
2-(o-Ethoxycarbonylmethylsulfinylphenyl)imidazo(4,5-c)pyridine.

2-(m-Ethoxycarbonylmethylsulfinylphenyl)imidazo(4,5-c)pyridine.
2-(p-Ethoxycarbonylmethylsulfinylphenyl)imidazo(4,5-c)pyridine.
2-(2-Hydroxy-4-methoxyphenyl)imidazo(4,5-c)pyridine.
2-(4-Hydroxy-2-methoxyphenyl)imidazo(4,5-c)pyridine, fumarate, m.p. 255°.
2-(2-Ethoxy-4-hydroxyphenyl)imidazo(4,5-c)pyridine.
2-(4-Ethoxy-2-hydroxyphenyl)imidazo(4,5-c)pyridine.
2-(2-Ethoxy-4-methoxyphenyl)imidazo(4,5-c)pyridine, fumarate, m.p. 198°.
2-(4-Ethoxy-2-methoxyphenyl)imidazo(4,5-c)pyridine, fumarate, m.p. 213°.
2-(2,4-Diethoxyphenyl)imidazo(4,5-c)pyridine.
2-(2-Isopropyloxy-4-methoxyphenyl)imidazo(4,5-c)pyridine.
2-(4-Isopropyloxy-2-methoxyphenyl)imidazo(4,5-c)pyridine, bis-fumarate, m.p. 220°.
2-(2,4-Diisopropyloxyphenyl)imidazo(4,5-c)pyridine.
2-(2-Allyloxy-4-hydroxyphenyl)imidazo(4,5-c)pyridine.
2-(4-Allyloxy-2-hydroxyphenyl)imidazo(4,5-c)pyridine.
2-(2-Allyloxy-4-methoxyphenyl)imidazo(4,5-c)pyridine, hydrochloride, m.p. 206°.
2-(4-Allyloxy-2-methoxyphenyl)imidazo(4,5-c)pyridine, hydrochloride, m.p. 250°,
2-(2-Allyloxy-4-ethoxyphenyl)imidazo(4,5-c)pyridine.
2-(4-Allyloxy-2-ethoxyphenyl)imidazo(4,5-c)pyridine.
2-(2-Allyloxy-4-isopropoxyphenyl)imidazo(4,5-c)pyridine.
2-(4-Allyloxy-2-isopropoxyphenyl)imidazo(4,5-c)pyridine.
2-(2,4-Bisallyloxyphenyl)imidazo(4,5-c)pyridine, hydrochloride, m.p. 179°.
2-(2-Hydroxy-4-propargyloxyphenyl)imidazo(4,5-c)pyridine.
2-(3-Hydroxy-4-propargyloxyphenyl)imidazo(4,5-c)pyridine.
2-(4-Hydroxy-2-propargyloxyphenyl)imidazo(4,5-c)pyridine.
2-(2-Methoxy-3-propargyloxyphenyl)imidazo(4,5-c)pyridine, hydrochloride, m.p. 242°.
2-(2-Methoxy-4-propargyloxyphenyl)imidazo(4,5-c)pyridine.
2-(2-Methoxy-5-propargyloxyphenyl)imidazo(4,5-c)pyridine, fumarate, m.p. 210°.
2-(2-Methoxy-6-propargyloxyphenyl)imidazo(4,5-c)pyridine.
2-(3-Methoxy-2-propargyloxyphenyl)imidazo(4,5-c)pyridine.
2-(3-Methoxy-4-propargyloxyphenyl)imidazo(4,5-c)pyridine.
2-(3-Methoxy-5-propargyloxyphenyl)imidazo(4,5-c)pyridine.
2-(3-Methoxy-6-propargyloxyphenyl)imidazo(4,5-c)pyridine.
2-(4-Methoxy-2-propargyloxyphenyl)imidazo(4,5-c)pyridine, fumarate, m.p. 210°.
2-(4-Methoxy-3-propargyloxyphenyl)imidazo(4,5-c)pyridine.
2-(2-Ethoxy-3-propargyloxyphenyl)imidazo(4,5-c)pyridine.
2-(2-Ethoxy-4-propargyloxyphenyl)imidazo(4,5-c)pyridine.
2-(2-Ethoxy-5-propargyloxyphenyl)imidazo(4,5-c)pyridine.
2-(2-Ethoxy-6-propargyloxyphenyl)imidazo(4,5-c)pyridine.
2-(3-Ethoxy-2-propargyloxyphenyl)imidazo(4,5-c)pyridine.
2-(3-Ethoxy-4-propargyloxyphenyl)imidazo(4,5-c)pyridine.
2-(3-Ethoxy-5-propargyloxyphenyl)imidazo(4,5-c)pyridine.
2-(4-Ethoxy-2-propargyloxyphenyl)imidazo(4,5-c)pyridine.
2-(4-Ethoxy-3-propargyloxyphenyl)imidazo(4,5-c)pyridine.
2-(3,5-Dimethoxy-4-propargyloxyphenyl)imidazo(4,5-c)pyridine, dihydrochloride, m.p. 238°.
2-(3,5-Diethoxy-4-propargyloxyphenyl)imidazo(4,5-c)pyridine.
2-(2-Allyloxy-4-propargyloxyphenyl)imidazo(4,5-c)pyridine.
2-(3-Allyloxy-4-propargyloxyphenyl)imidazo(4,5-c)pyridine.
2-(4-Allyloxy-2-propargyloxyphenyl)imidazo(4,5-c)pyridine.
2-(2,4-Bispropargyloxyphenyl)imidazo(4,5-c)pyridine, fumarate, m.p. 195°.
2-[2-Hydroxy-4-(2-hydroxyethoxy)-phenyl]imidazo(4,5-c)pyridine.
2-[4-Hydroxy-2-(2-hydroxyethoxy)-phenyl]imidazo(4,5-c)pyridine.
2-[2-(2-Hydroxyethoxy)-4-methoxyphenyl]imidazo(4,5-c)pyridine, hydrochloride, m.p. 250°.
2-[4-(2-Hydroxyethoxy)-4-methoxyphenyl]imidazo(4,5-c)pyridine.
2-[2-Ethoxy-4-(2-hydroxyethoxy)-phenyl]imidazo(4,5-c)pyridine.
2-[4-Ethoxy-2-(2-hydroxyethoxy)-phenyl]imidazo(4,5-c)pyridine.
2-[2-Allyloxy-4-(2-hydroxyethoxy)-phenyl]imidazo(4,5-c)pyridine.
2-[4-Allyloxy-2-(2-hydroxyethoxy)-phenyl]imidazo(4,5-c)pyridine.
2-[2-(2-Hydroxyethoxy)-4-propargyloxyphenyl]imidazo(4,5-c)pyridine.
2-[4-(2-Hydroxyethoxy)-2-propargyloxyphenyl]imidazo(4,5-c)pyridine.
2-[2,4-Bis(2-hydroxyethoxy)phenyl]imidazo(4,5-c)pyridine.
2-(2-Cyanomethoxy-4-hydroxyphenyl)imidazo(4,5-c)pyridine.
2-(4-Cyanomethoxy-2-hydroxyphenyl)imidazo(4,5-c)pyridine.
2-(2-Cyanomethoxy-4-methoxyphenyl)imidazo(4,5-c)pyridine.
2-(4-Cyanomethoxy-2-methoxyphenyl)imidazo(4,5-c)pyridine, fumarate, m.p. 198°.
2-(2-Cyanomethoxy-4-ethoxyphenyl)imidazo(4,5-c)pyridine.
2-(4-Cyanomethoxy-2-ethoxyphenyl)imidazo(4,5-c)pyridine.
2-(2-Allyloxy-4-cyanomethoxyphenyl)imidazo(4,5-c)pyridine.
2-(4-Allyloxy-2-cyanomethoxyphenyl)imidazo(4,5-c)pyridine.
2-(2-Cyanomethoxy-4-propargyloxyphenyl)imidazo(4,5-c)pyridine.
2-(4-Cyanomethoxy-2-propargyloxyphenyl)imidazo(4,5-c)pyridine.
2-[2-Cyanomethoxy-4-(2-hydroxyethoxy)-phenyl]imidazo(4,5-c)pyridine.
2-[4-Cyanomethoxy-2-(2-hydroxyethoxy)-phenyl]imidazo(4,5-c)pyridine.

2-(2,4-Biscyanomethoxyphenyl)imidazo(4,5-c)pyridine.
2-(4-Carboxymethoxy-2-hydroxyphenyl)imidazo(4,5-c)pyridine.
2-(4-Carboxymethoxy-2-methoxyphenyl)imidazo(4,5-c)-pyridine, m.p. 235°, hydrochloride, m.p. 252°.
2-(4-Carboxymethoxy-2-ethoxyphenyl)imidazo(4,5-c)pyridine.
2-(2-Allyloxy-4-carboxymethoxyphenyl)imidazo(4,5-c)pyridine.
2-(2,4-Biscarboxymethoxyphenyl)imidazo(4,5-c)pyridine.
2-(2-Carboxymethoxy-4-propargyloxyphenyl)imidazo(4,5-c)pyridine.
2-(4-Carboxymethoxy-2-propargyloxyphenyl)imidazo(4,5-c)pyridine.
2-(4-Methoxycarbonylmethoxy-2-hydroxyphenyl)imidazo(4,5-c)pyridine.
2-(4-Methoxycarbonylmethoxy-2-methoxyphenyl)imidazo(4,5-c)pyridine.
2-(2-Ethoxy-4-methoxycarbonylmethoxyphenyl)imidazo(4,5-c)pyridine.
2-(2-Allyloxy-4-methoxycarbonylmethoxyphenyl)imidazo(4,5-c)pyridine.
2-(2,4-Bismethoxycarbonylmethoxyphenyl)imidazo(4,5-c)pyridine.
2-(2-Methoxycarbonylmethoxy-4-propargyloxyphenyl)imidazo(4,5-c)pyridine.
2-(4-Methoxycarbonylmethoxy-2-propargyloxyphenyl)imidazo(4,5-c)pyridine.
2-(4-Ethoxycarbonylmethoxy-2-hydroxyphenyl)imidazo(4,5-c)pyridine.
2-(4-Ethoxycarbonylmethoxy-2-methoxyphenyl)imidazo(4,5-c)pyridine.
2-(2-Ethoxy-4-ethoxycarbonylmethoxyphenyl)imidazo(4,5-c)pyridine.
2-(2-Allyloxy-4-ethoxycarbonylmethoxyphenyl)imidazo(4,5-c)pyridine.
2-(2,4-Bisethoxycarbonylmethoxyphenyl)imidazo(4,5-c)pyridine.
2-(2-Ethoxycarbonylmethoxy-4-propargyloxyphenyl)imidazo(4,5-c)pyridine.
2-(4-Ethoxycarbonylmethoxy-2-propargyloxyphenyl)imidazo(4,5-c)pyridine.
2-(4-Mercapto-2-methoxyphenyl)imidazo(4,5-c)pyridine.
2-(2-Mercapto-4-propargyloxyphenyl)imidazo(4,5-c)pyridine.
2-(2-Hydroxy-4-methylthiophenyl)imidazo(4,5-c)pyridine.
2-(4-Hydroxy-2-methylthiophenyl)imidazo(4,5-c)pyridine.
2-(2-Methoxy-4-methylthiophenyl)imidazo(4,5-c)pyridine, hydrochloride, m.p. 253°.
2-(2-Methoxy-5-methylthiophenyl)imidazo(4,5-c)pyridine, hydrochloride, m.p. 242°.
2-(4-Methoxy-2-methylthiophenyl)imidazo(4,5-c)pyridine.
2-(2-Ethoxy-4-methylthiophenyl)imidazo(4,5-c)pyridine.
2-(4-Ethoxy-2-methylthiophenyl)imidazo(4,5-c)pyridine.
2-(2-Allyloxy-4-methylthiophenyl)imidazo(4,5-c)pyridine.
2-(4-Allyloxy-2-methylthiophenyl)imidazo(4,5-c)pyridine.
2-(2-Methylthio-4-propargyloxyphenyl)imidazo(4,5-c)pyridine.
2-(4-Methylthio-2-propargyloxyphenyl)imidazo(4,5-c)pyridine.
2-(2-Cyanomethoxy-4-methylthiophenyl)imidazo(4,5-c)pyridine.
2-(4-Cyanomethoxy-2-methylthiophenyl)imidazo(4,5-c)pyridine.
2-(2,4-Bismethylthiophenyl)imidazo(4,5-c)pyridine.
2-(4-Ethylthio-2-methoxyphenyl)imidazo(4,5-c)pyridine, hydrochloride. m.p. 262°.
2-(2-Methoxy-4-propylthiophenyl)imidazo(4,5-c)pyridine.
2-(4-Allylthio-2-methoxyphenyl)imidazo(4,5-c)pyridine.
2-(2-Methoxy-4-propargylthiophenyl)imidazo(4,5-c)pyridine.
2-(4-Cyanomethylthio-2-methoxyphenyl)imidazo(4,5-c)pyridine.
2-(4-Carboxymethylthio-2-methoxyphenyl)imidazo(4,5-c)pyridine.
2-(4-Methoxycarbonylmethylthio-2-methoxyphenyl)imidazo(4,5-c)pyridine.
2-(4-Ethoxycarbonylmethylthio-2-methoxyphenyl)imidazo(4,5-c)pyridine.
2-(2-Hydroxy-4-methylsulfinylphenyl)imidazo(4,5-c)pyridine.
2-(4-Hydroxy-2-methylsulfinylphenyl)imidazo(4,5-c)pyridine.
2-(2-Methoxy-4-methylsulfinylphenyl)imidazo(4,5-c)pyridine, fumarate, m.p. 215°.
2-(4-Methoxy-2-methylsulfinylphenyl)imidazo(4,5-c)pyridine.
2-(2-Ethoxy-4-methylsulfinylphenyl)imidazo(4,5-c)pyridine.
2-(4-Ethoxy-2-methylsulfinylphenyl)imidazo(4,5-c)pyridine.
2-(2-Allyloxy-4-methylsulfinylphenyl)imidazo(4,5-c)pyridine.
2-(4-Allyloxy-2-methylsulfinylphenyl)imidazo(4,5-c)pyridine.
2-(2-Methylsulfinyl-4-propargyloxyphenyl)imidazo(4,5-c)pyridine.
2-(4-Methylsulfinyl-2-propargyloxyphenyl)imidazo(4,5-c)pyridine.
2-(2-Cyanomethoxy-4-methylsulfinylphenyl)imidazo(4,5-c)pyridine.
2-(4-Cyanomethoxy-2-methylsulfinylphenyl)imidazo(4,5-c)pyridine.
2-(2,4-Bismethylsulfinylphenyl)imidazo(4,5-c)pyridine.
2-(4-Ethylsulfinyl-2-methoxyphenyl)imidazo(4,5-c)pyridine.
2-(2-Methoxy-4-propylsulfinylphenyl)imidazo(4,5-c)pyridine.
2-(4-Allylsulfinyl-2-methoxyphenyl)imidazo(4,5-c)pyridine.
2-(2-Methoxy-4-propargylsulfinylphenyl)imidazo(4,5-c)pyridine.
2-(4-Cyanomethylsulfinyl-2-methoxyphenyl)imidazo(4,5-c)pyridine.
2-(4-Carboxymethylsulfinyl-2-methoxyphenyl)imidazo(4,5-c)pyridine.
2-(4-Methoxycarbonylmethylsulfinyl-2-methoxyphenyl)imidazo(4,5-c)pyridine.
2-(4-Ethoxycarbonylmethylsulfinyl-2-methoxyphenyl)imidazo(4,5-c)pyridine.

EXAMPLE 2

A solution of 176 mg of p-propargyloxybenzoic acid in 1 ml of pyridine is treated with a solution of 109 mg of IIa in 1 ml of pyridine, the corresponding salt precipitating out. 0.19 ml of SOCl₂ is added dropwise at 0° with stirring; the mixture is stirred for 1 hour at 0° and 1 hour at 70°, concentrated and taken up with dilute hdyrochloric acid. The hydrochloride obtained is added to sodium carbonate solution and the precipitated 2-(p-propargyloxyphenyl)imidazo(4,5-b)-pyridine is filtered off. M.p. 218°.

EXAMPLE 3

2.06 g of 2-methoxy-4-propargyloxybenzoic acid is boiled off with 7 ml of benzene and 4 ml of thionyl chloride for 1 hour. The mixture is concentrated and dissolved in 5 ml of benzene. The solution of the acid chloride is added dropwise to a mixture of 1.09 g of IIa, 7 ml of pyridine and 5 ml of triethylamine. The mixture is stirred for 2 hours at 20°, treated with water, neutralized with hydrochloric acid and worked up as usual. The crude 2-amino-3-(2-methoxy-4-propargyloxybenzoylamino)pyridine obtained is converted into the hydrochloride and this (200 mg) is dissolved in 2 ml of pyridine. 0.2 ml of POCl₃ is added dropwise with stirring at 20°, and after 2 hours, the mixture is poured into water, worked up as usual and "M" is obtained.

EXAMPLE 4

A mixture of 10.9 g of IIa, 22 g of methyl 2-methoxy-4-propargyloxybenzoate and 300 ml of POCl₃ is heated at 120° for 2 hours, concentrated, and the residue is treated with 2N hydrochloric acid. "M" is obtained.

EXAMPLE 5

A mixture of 1.09 g of IIa, 1.87 g of 2-methoxy-4-propargyloxybenzonitrile and 3 g of p-toluenesulfonic acid monohydrate is treated at 160° for 3.5 hours. After cooling down, the mixture is worked up as usual and "M" is obtained.

EXAMPLE 6

A mixture of 4.33 g of S-methyl-2-methoxy-4-propargyloxythiobenzoic acid morpholide iodide (obtained by boiling 2-methoxy-4-propargyloxybenzaldehyde with sulfur in morpholine and subsequent reaction with CH₃I in acetone), 1.09 g of IIa and 35 ml of ethylene glycol is heated for 40 minutes at 130°, poured into ice water, filtered and "M" is obtained.

EXAMPLE 7

1.09 g of IIa and 3 g of 2-methoxy-4-propargyloxybenzoic anhydride are heated at 180° for 5 hours, the mixture is cooled down and worked up as usual and "M" is obtained.

EXAMPLE 8

2.78 g of 2-methoxy-4-propargyloxybenzoic acid morpholide is mixed with 1.09 g of IIa, 5 ml of POCl₃ is added dropwise with stirring, the mixture is boiled for 3 hours and concentrated. After the usual work-up, "M" is obtained.

EXAMPLE 9

1.09 of IIa, 3.11 g of 2-methoxy-4-propargyloxybenzoic acid morpholide imide chloride, 6 ml of triethylamine and 5 ml of diethylene glycol dimethyl ether are heated at 120° for 30 minutes. After cooling, the mixture is worked up as usual and "M" is obtained.

EXAMPLE 10

10.9 of IIa, 19 g of 2-methoxy-4-propargyloxybenzaldehyde (obtained from 2,4-dihydroxybenzaldehyde via 2-hydroxy-4-propargyloxybenzaldehyde) and 10 g of sulfur are stirred in 200 ml of mesitylene at 180° for 10 hours, the mixture is concentrated, extracted with methanol, filtered and the solution is concentrated to 350 ml. "M" precipitates out on addition of ethereal hydrochloric acid.

EXAMPLE 11

10 g IIa and 19 g of 2-methoxy-4-propargyloxybenzaldehyde are dissolved in 100 ml of dimethylacetamide, and, after the addition of 19 g of sodium bisulfite, the mixture is stirred for 2 hours at 140°, then worked up as usual and "M" is obtained.

In analogy to Example 10 or 11, the compounds given in Example 1 are obtained from IIa or from 3,4-diaminopyridine with the appropriate aldehydes (such as, for example, p-propargyloxybenzaldehyde, m.p. 80°; m-propargyloxybenzaldehyde, oil; 2-methoxy-4-ethoxycarbonylmethoxybenzaldehyde, m.p. 88°).

EXAMPLE 12

24.1 g of 2-(4-hydroxy-2-methoxyphenyl)imidazo(4-5-b)pyridine [hydrochloride, m.p. 255°; obtainable by condensation of II with 4-benzyloxy-2-methoxybenzoic acid (m.p. 130°) to give 2-(4-benzyloxy-2-methoxyphenyl)imidazo(4,5-b)pyridine (hydrochloride, m.p. 244°) and subsequent hydrogenolysis] is dissolved in the calculated amount of 2N sodium hydroxide solution, the solution is concentrated and residual water is removed by twice adding toluene and concentrating. The Na salt obtained is taken up to 300 ml of dimethylformamide, treated with 8 ml of propargyl chloride and stirred at 20° for 16 hours. The mixture is worked up as usual with water and ethyl acetate and "M" is obtained.

Analogously, the ethers given in Example 1 are obtained by etherification from the appropriate hydroxy compounds.

EXAMPLE 13

A mixture of 10 g of 2-(4-acetoxy-2-methoxyphenyl)imidazo(4,5-c)pyridine, 100 ml of methanol and 100 ml of 2N aqueous NaOH solution is allowed to stand at 20° for 16 hours. After the usual work-up, 2-(4-hydroxy-2-methoxyphenyl)imidazo(4,5-c)pyridine is obtained; fumarate, m.p. 255°.

Analogously, the hydroxy compounds mentioned in Example 1 are obtained by alkaline hydrolysis of the appropriate acetoxy compounds.

EXAMPLE 14

A solution of 10 g of 2-(4-benzyloxy-2-methoxyphenyl)imidazo(4,5-c)pyridine hydrochloride (m.p. 241°; obtained by condensation of IIb with 4-benzyloxy-2-methoxybenzoic acid) is hydrogenated in 150 ml of methanol on 5 g of 5% Pd-C at 20° and 1 bar until hydrogen uptake is complete, the mixture is filtered, worked up as usual and 2-(4-hydroxy-2-methoxyphenyl)imidazo(4,5-c)pyridine is obtained; fumarate, m.p. 255°

Analogously, the hydroxy and mercapto compounds mentioned in Example 1 are obtained by hydrogenolysis of the appropriate benzyl ethers or benzyl thioethers respectively.

EXAMPLE 15

In analogy to Example 12, 2-(2-methoxy-4-methylthiophenyl)imidazo(4,5-c)pyridine hydrochloride, m.p. 253°, is obtained by converting 2-(4-mercapto-2-methoxyphenyl)imidazo(4,5-c)pyridine into the Na salt and subsequent reaction with methyl iodide.

Analogously, the thioethers described in Example 1 are obtained from the appropriate mercapto compounds by thioetherification.

EXAMPLE 16

10 ml of 30% $H_2O_2$ is added to a boiling solution of 2.71 g of 2-(2-methoxy-4-methylthiophenyl)imidazo(4,5-c)pyridine in 50 ml of ethanol, and the mixture is then boiled for 3 hours. After cooling down and the usual work-up, 2-(2-methoxy-4-methylsulphinylphenyl)imidazo(4,5-c)pyridine fumarate, m.p. 215°, is obtained.

Analogously, the sulfinyl compounds described in Example 1 are obtained by oxidation of the appropriate thioethers.

EXAMPLE 17

1 g of 2-(4-ethoxycarbonylmethoxy-2-methoxyphenyl)imidazo(4,5-c)pyridine is dissolved in 25 ml of 2N aqueous-ethanolic KOH and the mixture is allowed to stand at 20° for 1 hour. After acidification with hydrochloric acid, the mixture is worked up as usual and 2-(4-carboxymethoxy-2-methoxyphenyl)imidazo(4,5-c)pyridine is obtained, m.p.235°.

Analogously, the carboxylic acids mentioned in Example 1 are obtained by hydrolysis of the appropriate esters.

EXAMPLE 18

1 g of 2-(4-carboxymethoxy-2-methoxyphenyl)imidazo(4,5-b) pyridine is dissolved in 20 ml of ethanol, the solution is saturated with HCl gas and allowed to stand overnight. After concentration and the usual work-up, 2-(4-ethoxycarbonylmethoxy-2-methoxyphenyl)imidazo(4,5-b)pyridine is obtained; hemifumarate, m.p. 198°.

Analogously, the esters mentioned in Example 1 are obtained by esterification of the appropriate carboxylic acids.

The following examples relate to pharmaceutical formulations which contain compounds of formula I or their acid addition salts:

Example A: Tablets

A mixture of 1 kg of "M", 4 kg of lactose, 1.2 kg of potato starch, 0.2 kg of talc and 0.1 kg of magnesium stearate is pressed into tablets in a customary manner so that each tablet contains 100 mg of active ingredient.

Example B: Coated Tablets

In analogy to Example A, tablets are pressed and then are coated in a customary manner with a coating consisting of sucrose, potato starch, talc, tragacanth and dye.

Example C: Capsules 10 kg of "M" is filled in a customary manner into hard gelatine capsules, so that each capsule contains 50 mg of active ingredient.

Example D: Ampoules

A solution of 1 kg of "M" in 100 l of double-distilled water is filtered sterile, filled into ampoules, lyophilized under sterile conditions and sealed sterile. Each ampoule contains 50 mg of active ingredient.

In analogy, tablets, coated tablets, capsules and ampoules can be obtained which contain one or more of the other active ingredients of formula I and/or their physiologically acceptable acid addition salts.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 2-arylimidazopyridine of the formula

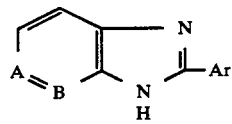

wherein

—A═B— is (a) —CH═N— or (b) —N═CH—,

Ar is phenyl which, in case (a), is substituted by one or two alkynyloxy, cyanomethoxy, or alkyloxycarbonylmethoxy groups, and can also be substituted additionally by one of two hydroxyl, alkyloxy, alkenyloxy or alkynyloxy groups, or in case (b), is substituted by one to three mercapto, or —Z—R groups, Z is —O—, —S— or —SO—, and R is alkyl, alkenyl, alkynyl, hydroxyalkyl, cyanomethyl, carboxymethyl, or alkyloxycarbonylmethyl, the alkyl, alkenyl, alkynyl and hydroxyalkyl groups throughout the above, each having up to 5 C atoms, with the proviso that, in case (b), the phenyl radical is only substituted by methoxy if it has at least one other substituent differing from methoxy, or a physiologically acceptable salt thereof.

2. A compound of claim 1 wherein —A═B— is —N═CH—.

3. A compound of claim 1 wherein Ar is phenyl substituted by a propargyloxy, cyanomethoxy, or alkyloxycarbonylmethoxy group and can also be substituted additionally by one or two additional alkyloxy groups or by an additional allyloxy or propargyloxy group, the alkyloxy groups each having 1-3 C atoms.

4. A compound of claim 2 wherein Ar is phenyl substituted by an ethoxy, propyloxy, isopropyloxy, allyloxy, propargyloxy, 2-hydroxyethoxy, cyanomethoxy, carboxymethoxy, alkyloxycarbonylmethoxy, methylthio or methylsulfinyl group and can also be substituted additionally by an additional alkyloxy, allyloxy or propargyloxy group, the alkyloxy groups having in each case 1-3 C atoms.

5. A compound of claim 1 wherein Ar is phenyl which is substituted by one or two alkynyloxy, cyanomethoxy or alkyloxycarbonylmethoxy groups, and can also be substituted additionally by one or two alkyloxy, alkenyloxy or alkynyloxy groups, the alkyl, alkenyl and alkynyl groups each having up to 5 C atoms, or a physiologically acceptable salt thereof.

6. A compound of claim 2 wherein Ar is phenyl which is substituted by one or two carboxymethoxy groups, and can also be substituted additionally by one or two alkyloxy, alkenyloxy or alkynyloxy groups, the alkyl, alkenyl and alkynyl groups each having up to 5 C atoms, or a physiologically acceptable salt thereof.

7. A compound of claim 2, wherein one Z is S.

8. A compound of claim 2, wherein one Z is SO.

9. 2-(2-methoxy-4-methylthiophenyl)imidazo(4,5-c)-pyridine, or a physiologically acceptable salt thereof, compounds of claim 2.

10. 2-(2-methoxy-4-methylsulfinylphenyl)imidazo(4,5-c)-pyridine, or a physiologically acceptable salt thereof.

11. A compound of claim 7, wherein one ZR is alkoxy.

12. A compound of claim 8, wherein one ZR is alkoxy.

13. 2-(2-Methoxy-4-propargyloxyphenyl)imidazo(4,5-b)-pyridine, a compound of claim 1.

14. 2-(4-Cyanomethoxy-2-methoxyphenyl)imidazo(4,5-b)-pyridine, a compound of claim 1.

15. 2-(4-Allyloxy-2-methoxyphenyl)imidazo(4,5-c)-pyridine, a compound of claim 1.

16. 2-(2-Methoxy-4-propargyloxyphenyl)imidazo(4,5-c)-pyridine, a compound of claim 1.

17. A pharmaceutical composition comprising a compound of the formula

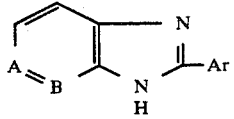

wherein

—A=B— is (a) —CH=N— or (b) —N=CH—,

Ar is phenyl which, in case (a), is substituted by one or two alkynyloxy, cyanomethoxy, carboxymethoxy, or alkyloxycarbonylmethoxy groups, and can also be substituted additionally by one or two hydroxyl, alkyloxy, alkenyloxy or alkynyloxy groups, or in case (b), is substituted by one to three hydroxyl, mercapto, or —Z—R groups, Z is —O—, —S— or —SO—, and R is alkyl, alkenyl, alkynyl, hydroxyalkyl, cyanomethyl, carboxymethyl, or alkyloxycarbonylmethyl, the alkyl, alkenyl, alkynyl and hydroxyalkyl groups throughout the above, each having up to 5 C atoms, with the proviso that, in case (b), the phenyl radical is only substituted by hydroxyl if it has at least one other substituent differing from hydroxy, and is only substituted by methoxy if it has at least one other substitutent differing from methoxy, or a physiologically acceptable salt thereof and a pharmaceutically acceptable carrier.

18. A pharmaceutical composition of claim 17 wherein the amount of active ingredient is 10–500 mg.

19. A pharmaceutical composition comprising a compound of claim 9 and a pharmaceutically acceptable carrier.

20. A pharmaceutical composition comprising a compound of claim 10 and a pharmaceutically acceptable carrier.

21. A method of treating cardiac insufficiency in a patient in need of such treatment comprising administering to the patient an amount of a compound of the formula

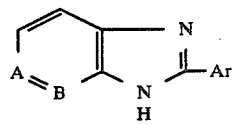

wherein

—A=B— is (a) —CH=N— or (b) —N=CH—,

Ar is phenyl which, in case (a), is substituted by one or two alkynyloxy, cyanomethoxy, carboxymethoxy, or alkyloxycarbonylmethoxy groups, and can also be substituted additionally by one or two hydroxyl, alkyloxy, alkenyloxy or alkynyloxy groups, or in case (b), is substituted by one to three hydroxyl, mercapto, or —Z—R groups, Z is —O—, —S— or —SO—, and R is alkyl, alkenyl, alkynyl, hydroxyalkyl, cyanomethyl, carboxymethyl, or alkyloxycarbonylmethyl, the alkyl, alkenyl, alkynyl and hydroxyalkyl groups throughout the above, each having up to 5 C atoms, with the proviso that, in case (b), the phenyl radical is only substituted by hydroxyl if it has at least one other substituent differing from hydroxy, and is only substituted by methoxy if it has at least one other substitutent differing from methoxy, or a physiologically acceptable salt thereof.

22. A method of achieving an anti-hypertensive effect comprising administering a compound of the formula

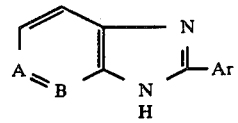

wherein

—A=B— is (a) —CH=N— or (b) —N=CH—,

Ar is phenyl which, in case (a), is substituted by one or two alkynyloxy, cyanomethoxy, carboxymethoxy, or alkyloxycarbonylmethoxy groups, and can also be substituted additionally by one or two hydroxyl, alkyloxy, alkenyloxy or alkynyloxy groups, or in case (b), is substituted by one to three hydroxyl, mercapto, or —Z—R groups, Z is —O—, —S— or —SO—, and R is alkyl, alkenyl, alkynyl, hydroxyalkyl, cyanomethyl, carboxymethyl, or alkyloxycarbonylmethyl, the alkyl, alkenyl, alkynyl and hydroxyalkyl groups throughout the above, each having up to 5 C atoms, with the proviso that, in case (b), the phenyl radical is only substituted by hydroxyl if it has at least one other substituent differing from hydroxy, and is only substituted by methoxy if it has at least one other substituent differing from methoxy, or a physiologically acceptable salt thereof.

23. A method of achieving a positive inotropic effect comprising administering a compound of the formula

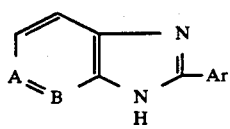

wherein

—A=B— is (a) —CH=N— or (b) —N=CH—,

Ar is phenyl which, in case (a), is substituted by one or two alkynyloxy, cyanomethoxy, carboxymethoxy, or alkyloxycarbonylmethoxy groups, and can also be substituted additionally by one or two hydroxyl, alkyloxy, alkenyloxy or alkynyloxy groups, or in case (b), is substituted by one to three hydroxyl, mercapto, or —Z—R groups, Z is —O—, —S— or —SO—, and R is alkyl, alkenyl, alkynyl, hydroxyalkyl, cyanomethyl, carboxymethyl, or alkyloxycarbonylmethyl, the alkyl, alkenyl, alkynyl and hydroxyalkyl groups throughout the above, each having up to 5 C atoms, with the proviso that, in case (b), the phenyl radical is only substituted by hydroxyl if it has at least one other substituent differing from hydroxy, and is only substituted differing by methoxy if it has at least one other substituent from methoxy, or a physiologically acceptable salt thereof.

24. A method of achieving a positive inotropic effect, comprising administering a compound of claim 10.

25. A method of treating cardiac insufficiency, comprising administering a compound of claim 10.

26. A method of treating hypertension, comprising administering a compound of claim 10.

27. A method of treating an ulcer, comprising administering a compound of claim 10.

28. A method of achieving a positive inotropic effect, comprising administering a compound of claim 9.

29. A method of treating cardiac insufficiency, comprising administering a compound of claim 9.

30. A method of treating hypertension, comprising administering a compound of claim 9.

31. A method of treating an ulcer in a patient in need of such treatment comprising administering to the patient an amount of a compound of the formula

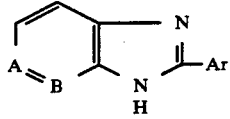

wherein

—A=B— is (a) —CH=N— or (b) —N=CH—,

Ar is phenyl which, in case (a), is substituted by one or two alkynyloxy, cyanomethoxy, carboxymethoxy, or alkyloxycarbonylmethoxy groups, and can also be substituted additionally by one or two hydroxyl, alkyloxy, alkenyloxy or alkynyloxy groups, or in case (b), is substituted by one to three hydroxyl, mercapto, or —Z—R groups, Z is —O—, —S— or —SO—, and R is alkyl, alkenyl, alkynyl, hydroxyalkyl, cyanomethyl, carboxymethyl, or alkyloxycarbonylmethyl, the alkyl, alkenyl, alkynyl and hydroxyalkyl groups throughout the above, each having up to 5 C atoms, with the proviso that, in case (b), the phenyl radical is only substituted by hydroxyl if it has at least one other substituent differing from hydroxy, and is only substituted differing by methoxy if it has at least one other substitutent from methoxy, or a physiologically acceptable salt thereof.

* * * * *